US012557988B2

(12) United States Patent
Huang et al.

(10) Patent No.: US 12,557,988 B2
(45) Date of Patent: Feb. 24, 2026

(54) OPTICAL PHYSIOLOGICAL SENSOR AND HEALTH MONITORING DEVICE USING THE SAME

(71) Applicant: HARVATEK CORPORATION, Hsinchu City (TW)

(72) Inventors: Shih-Jen Huang, Hsinchu City (TW); Po-Hsiang Huang, Hsinchu City (TW); Feng-Hui Chuang, New Taipei City (TW)

(73) Assignee: HARVATEK CORPORATION, Hsinchu City (TW)

( * ) Notice: Subject to any disclaimer, the term of this patent is extended or adjusted under 35 U.S.C. 154(b) by 372 days.

(21) Appl. No.: 18/349,931

(22) Filed: Jul. 10, 2023

(65) Prior Publication Data

US 2024/0335117 A1     Oct. 10, 2024

(30) Foreign Application Priority Data

Apr. 10, 2023    (TW) ................................ 112113202

(51) Int. Cl.
    *A61B 5/00*         (2006.01)
    *A61B 5/0205*       (2006.01)

(52) U.S. Cl.
    CPC ........ *A61B 5/0059* (2013.01); *A61B 5/02055* (2013.01); *A61B 2562/164* (2013.01)

(58) Field of Classification Search
    CPC ... A61B 5/0059; A61B 5/0205; A61B 5/6801; A61B 5/02055; A61B 5/02416; A61B 5/1455; A61B 5/14551; A61B 5/14552; A61B 2562/063; A61B 2562/164
    See application file for complete search history.

(56) References Cited

U.S. PATENT DOCUMENTS

| | | | | |
|---|---|---|---|---|
| 6,654,626 B2 * | 11/2003 | Devlin | ................... | A61B 5/291 |
| | | | | 600/397 |
| 2003/0225323 A1 * | 12/2003 | Kiani | ................. | A61B 5/14552 |
| | | | | 600/323 |
| 2007/0100219 A1 * | 5/2007 | Sweitzer | ............ | A61B 5/14551 |
| | | | | 600/323 |

(Continued)

FOREIGN PATENT DOCUMENTS

| | | |
|---|---|---|
| TW | I613419 B | 2/2018 |
| TW | 201825045 A | 7/2018 |
| TW | I735460 B | 8/2021 |

*Primary Examiner* — Chu Chuan Liu
(74) *Attorney, Agent, or Firm* — Li & Cai Intellectual Property Office

(57) ABSTRACT

An optical physiological sensor and a health monitoring device using the same are provided. The optical physiological sensor includes a module substrate, a light emitting module, and a detecting module. The module substrate includes a substrate, an electrode group, and a conductive path. The substrate has an emitting area, a receiving area, and an organism contact area between the emitting area and the receiving area. The electrode group is disposed on the organism contact area, and includes a first contact electrode, a second contact electrode, and a grounding electrode. The conductive path is configured to provide electrical conduction between the first contact electrode and the second contact electrode. The light emitting module is disposed on the emitting area. The detecting module is disposed on the receiving area.

14 Claims, 7 Drawing Sheets

(56)                    References Cited

U.S. PATENT DOCUMENTS

| | | | |
|---|---|---|---|
| 2008/0015424 A1* | 1/2008 | Bernreuter | A61B 5/14552 |
| | | | 600/323 |
| 2012/0083673 A1* | 4/2012 | Al-Ali | A61B 5/14553 |
| | | | 600/301 |
| 2020/0229725 A1* | 7/2020 | Ruskin | A61B 5/14552 |
| 2020/0237309 A1* | 7/2020 | Golda | A61B 5/0205 |

* cited by examiner

OPTICAL PHYSIOLOGICAL SENSOR AND HEALTH MONITORING DEVICE USING THE SAME

CROSS-REFERENCE TO RELATED PATENT APPLICATION

This application claims the benefit of priority to Taiwan Patent Application No. 112113202, filed on Apr. 10, 2023. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a sensor and an electronic device using the same, and more particularly to an optical physiological sensor and a health monitoring device using the same.

BACKGROUND OF THE DISCLOSURE

In recent years, people have paid more attention to health management, and the need for close monitoring of health conditions has increased during the covid-19 pandemic period. This leads to development of physiological monitoring devices, which can record important physiological parameters (e.g., human body temperatures, blood oxygen concentrations, heart rates, and an electrocardiogram) of a person to be detected in a non-invasive manner at any time, and can help alert or prevent possible changes in health status. The physiological monitoring devices are not only wearable on the person to be detected, but also available for vehicle mounted devices (e.g. seats) and long-term care devices (e.g. wheelchairs or mattresses).

The physiological monitoring devices are usually equipped with a light emitter and a light sensor that are modularized for monitoring physiological signals. The light emitter and the light sensor can be mounted on the same substrate to be packaged, and have a blocking wall disposed therebetween to prevent signal interference. Alternatively, each of the light emitter and the light sensor can be mounted on a substrate to be individually packaged, and a blocking wall is disposed around the light emitter. However, the wearable physiological monitoring devices are generally required to meet the design requirements of multifunctionality, miniaturization, and high integration. The conventional modularized designs of the light emitter and the light sensor fail to meet all the requirements and are considered to be lacking practical value.

SUMMARY OF THE DISCLOSURE

In response to the above-referenced technical inadequacies, the present disclosure provides an optical physiological sensor that is advantageous for miniaturized and integrated designs, and a health monitoring device using the same.

In order to solve the above-mentioned problems, one of the technical aspects adopted by the present disclosure is to provide an optical physiological sensor, which includes a module substrate, a light emitting module, and a detecting module. The module substrate includes a substrate, an electrode group, and a conductive path. The substrate has an emitting area, a receiving area, and an organism contact area between the emitting area and the receiving area. The electrode group is disposed on the organism contact area, and includes a first contact electrode, a second contact electrode, and a grounding electrode. The conductive path is configured to provide electrical conduction between the first contact electrode and the second contact electrode. The light emitting module is disposed on the emitting area, and includes at least one light emitting unit and a first packaging layer that covers the at least one light emitting unit. The detecting module is disposed on the receiving area, and includes at least one detecting unit and a second packaging layer that covers the at least one detecting unit.

In one of the possible or preferred embodiments, the substrate has a first surface and a second surface opposite to the first surface. The module substrate includes a protrusion disposed on the first surface of the organism contact area, and a height of the protrusion is greater than a height of the first packaging layer and the second packaging layer. The first contact electrode is disposed on a surface of the protrusion distant from the first surface. The second contact electrode and the grounding electrode are disposed on the second surface of the organism contact area. The conductive path passes through the organism contact area of the substrate and the protrusion.

In one of the possible or preferred embodiments, the module substrate has a conductive hole that penetrates through the organism contact area of the substrate and the protrusion, and the conductive hole is located between the first contact electrode and the second contact electrode to form the conductive path.

In one of the possible or preferred embodiments, the substrate has a first surface and a second surface opposite to the first surface. The first contact electrode is disposed on the first surface of the organism contact area. The second contact electrode and the grounding electrode are disposed on the second surface of the organism contact area. The conductive path passes through the organism contact area of the substrate.

In one of the possible or preferred embodiments, the module substrate has a conductive hole that penetrates through the organism contact area of the substrate, and the conductive hole is located between the first contact electrode and the second contact electrode to form the conductive path.

In one of the possible or preferred embodiments, the light emitting module includes a blocking wall disposed between the at least one light emitting unit and the protrusion. The at least one light emitting unit is configured to emit working light, and the blocking wall has a light transmittance of less than 5% with respect to the working light.

In one of the possible or preferred embodiments, the blocking wall is embedded in the first packaging layer.

In order to solve the above-mentioned problems, another one of the technical aspects adopted by the present disclosure is to provide a health monitoring device, which includes a functional module and an optical physiological sensor having the above-mentioned structure. The functional module is electrically connected to the optical physiological sensor. When the first contact electrode and the second contact electrode are in conduction with each other, the optical physiological sensor produces a wake-up signal to activate the functional module.

Therefore, in the optical physiological sensor and the health monitoring device provided by the present disclosure, by virtue of the substrate having an emitting area, a receiving area, and an organism contact area between the emitting area and the receiving area, the electrode group being disposed on the organism contact area and including a first contact electrode, a second contact electrode, and a grounding electrode, the conductive path being configured to provide electrical conduction between the first contact electrode and the second contact electrode, the light emitting module being disposed on the emitting area, and the detecting module being disposed on the receiving area, optical sensing and contact sensing (or contact wake-up) functions can be combined in the same module. Furthermore, the optical physiological sensor and the health monitoring device have the advantages of small footprint and high flexibility.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
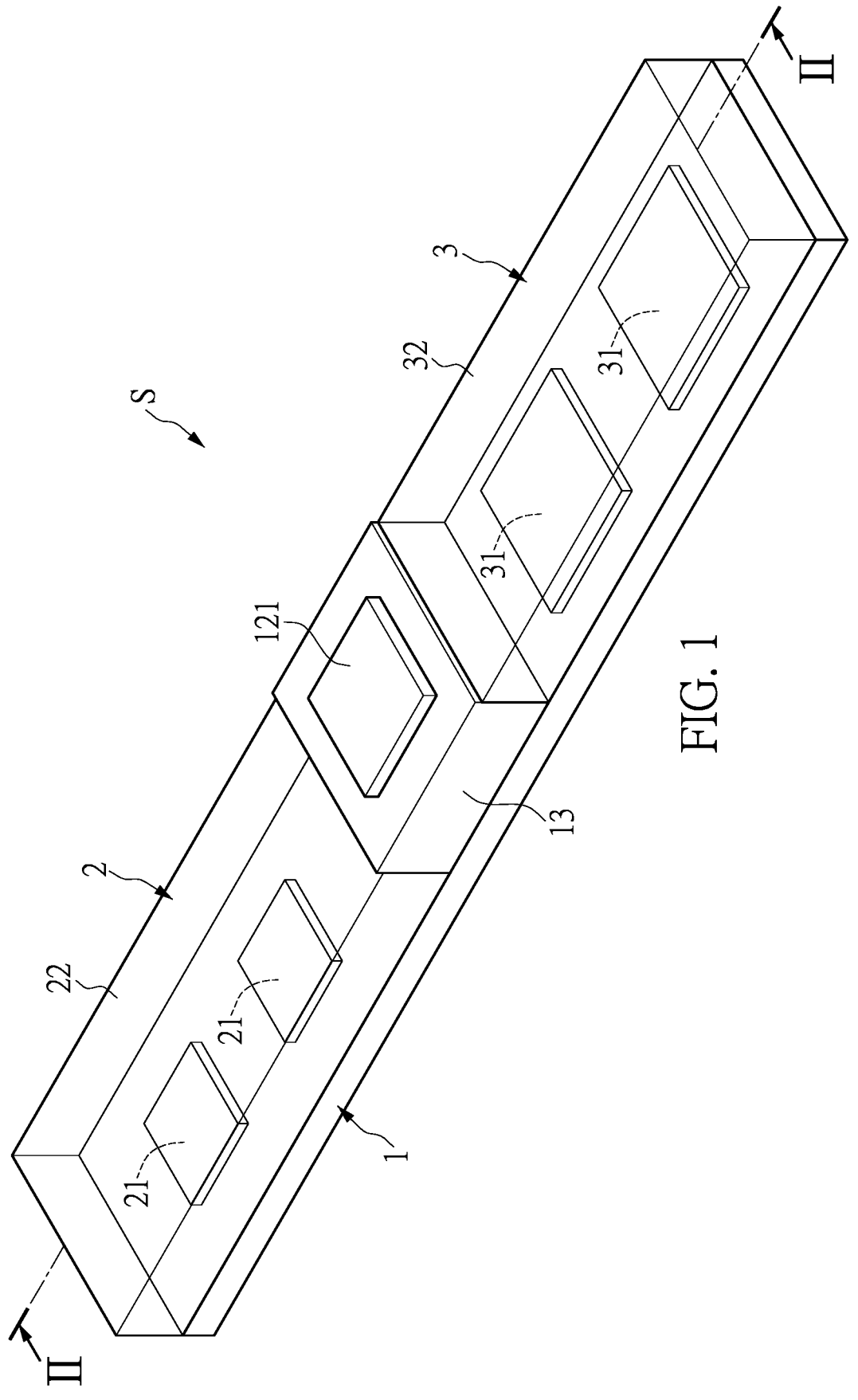
FIG. 1 is a schematic perspective view of an optical physiological sensor according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way.

Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Unless otherwise stated, the material(s) used in any described embodiment is/are commercially available material(s) or may be prepared by methods known in the art, and the process(es) or method(s) used in any described embodiment is/are conventional process(es) or method(s) generally known in the related art.

First Embodiment

Figure 2:
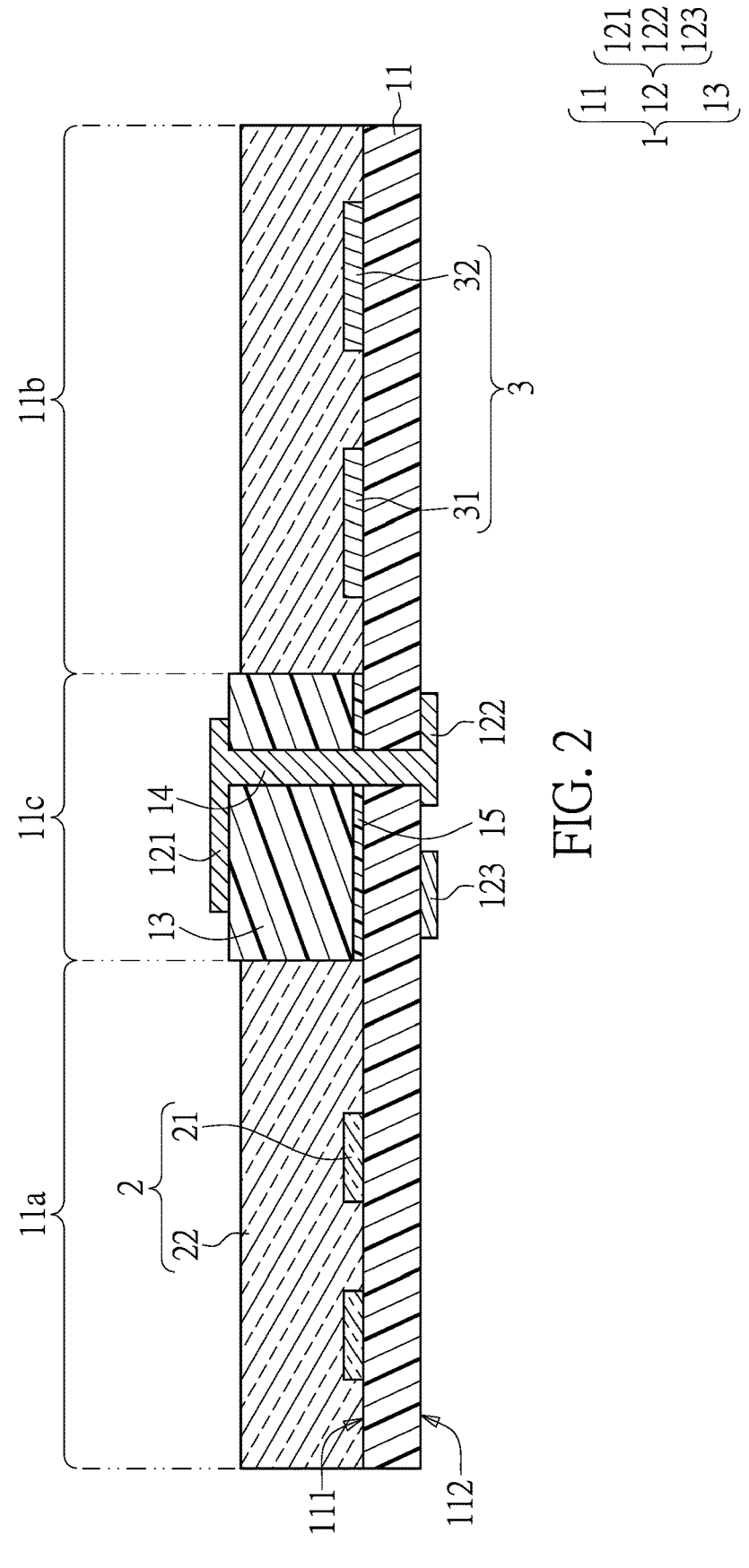
FIG. 2 is a schematic cross-sectional view taken along line II-II of FIG. 1.

Referring to FIG. 1 and FIG. 2, a first embodiment of the present disclosure provides an optical physiological sensor S, which includes a module substrate 1, a light emitting module 2, and a detecting module 3. The light emitting module 2 and the detecting module 3 are disposed on the module substrate 1. The light emitting module 2 is configured to emit light to an organism to be detected. The detecting module 3 is configured to receive the light reflected by the organism. Signals of the received light can be calculated or processed and be converted to corresponding physiological signals, so as to know physiological changes (e.g., blood oxygen concentration and heart rate changes) of the organism to be detected. It should be noted that, the module substrate 1 can be integrated with a contact sensing (or contact wake-up) function. In this way, through a direct skin contact, an electrocardiogram (ECG) signal of the organism to be detected can be obtained, or a wake-up signal to other function modules can be produced, thereby allowing a wide range of use and improving practicality.

In the present disclosure, the module substrate 1 includes a substrate 11, an electrode group 12, and a conductive path. The substrate 11 has an emitting area 11a, a receiving area 11b, and an organism contact area 11c between the emitting area 11a and the receiving area 11b. The electrode group 12 is disposed on the organism contact area 11c of the substrate 11, and includes a first contact electrode 121, a second contact electrode 122, and a grounding electrode 123. The conductive path is configured to provide electrical conduction between the first contact electrode 121 and the second contact electrode 122. The light emitting module 2 is disposed on the emitting area 11a, and includes at least one light emitting unit 21 and a first packaging layer 22 covering the at least one light emitting unit 21. The detecting module 3 is disposed on the receiving area 11b, and includes at least one detecting unit 31 and a second packaging layer 32 covering the at least one detecting unit 31.

It is worth mentioning that in the present embodiment, the electrode group 12 and the conductive path are constructed on the module substrate 1 by a protrusion 13 that can block side light interference of the at least one light emitting unit 21. More specifically, the substrate 11 has a first surface 111 (e.g., an upper surface) and a second surface 112 (e.g., a lower surface) opposite to the first surface 111. The protrusion 13 is disposed on the first surface 111 of the organism contact area 11c, and a height of the protrusion 13 is greater than a height of the first packaging layer 22 and the second packaging layer 32. The first contact electrode 121 is disposed on a surface of the protrusion 13 distant from the first surface 111. The second contact electrode 122 and the grounding electrode 123 are disposed on the second surface 112 of the organism contact area 11c. The conductive path passes through the organism contact area 11c of the substrate 11 and the protrusion 13.

In practice, the substrate 11 can be a printed circuit board having a predetermined circuit layout, which can be adjusted according to design requirements, and a plurality of connecting pads (not shown in FIG. 1 and FIG. 2) can be disposed on the first surface 111 and the second surface 112 for electrical connection. The substrate 11 and the protrusion 13 can be made of a bismaleimide triazine (BT) resin, and the protrusion 13 can be bonded to the substrate 11 by an adhesive layer 15, but the present disclosure is not limited thereto. Furthermore, the module substrate 1 has a conductive hole 14 that penetrates through the organism contact area 11c of the substrate 11 and the protrusion 13, and the conductive hole 14 is located between the first contact electrode 121 and the second contact electrode 122 to form the conductive path. The above description is provided for exemplary purposes only, and is not intended to limit the scope of the present disclosure.

The light emitting unit 21 can be a light emitting diode (LED) that emits visible light or invisible light, or any other types of light emitting element. The detecting unit 31 can be a light detector that matches with the light emitting unit 21, such as a photodiode or a phototransistor. However, such examples are not intended to limit the present disclosure. The first packaging layer 22 and the second packaging layer 32 are configured to allow light from the light emitting unit 21 to pass therethrough, and can respectively protect the light emitting unit 21 and the detecting unit 31 from physical damage and negative effects caused by surrounding environmental factors.

In the present embodiment, the first packaging layer 22 and the second packaging layer 32 can be formed from a transparent packaging material of an epoxy resin system or a silicone system, but are not limited thereto. The first packaging layer 22 and the second packaging layer 32 can be formed by compression molding, and the protrusion 13 can provide effective support to a mold during the compression molding process.

Figure 3:
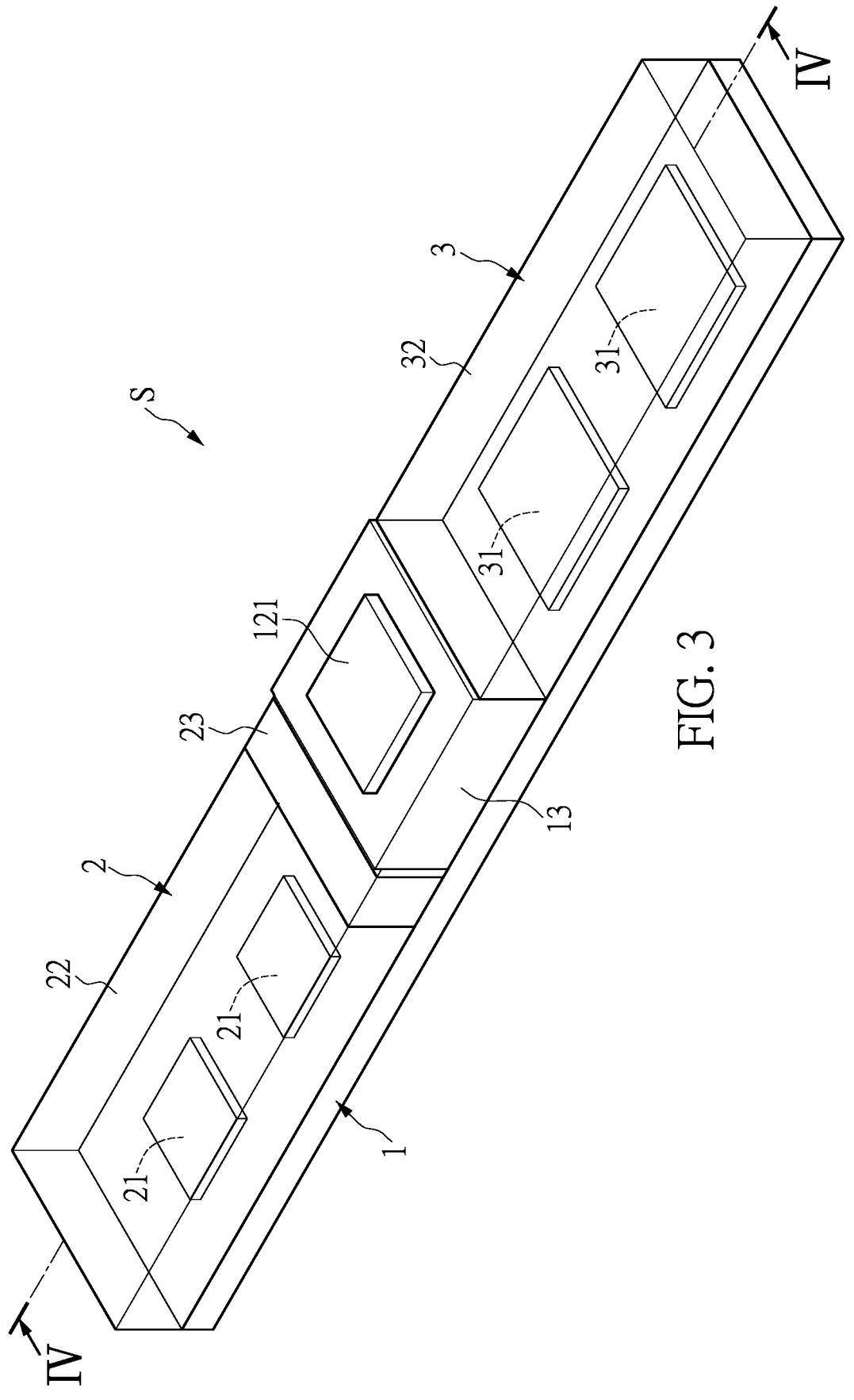
FIG. 3 is another schematic perspective view of the optical physiological sensor according to the first embodiment of the present disclosure.
Figure 4:
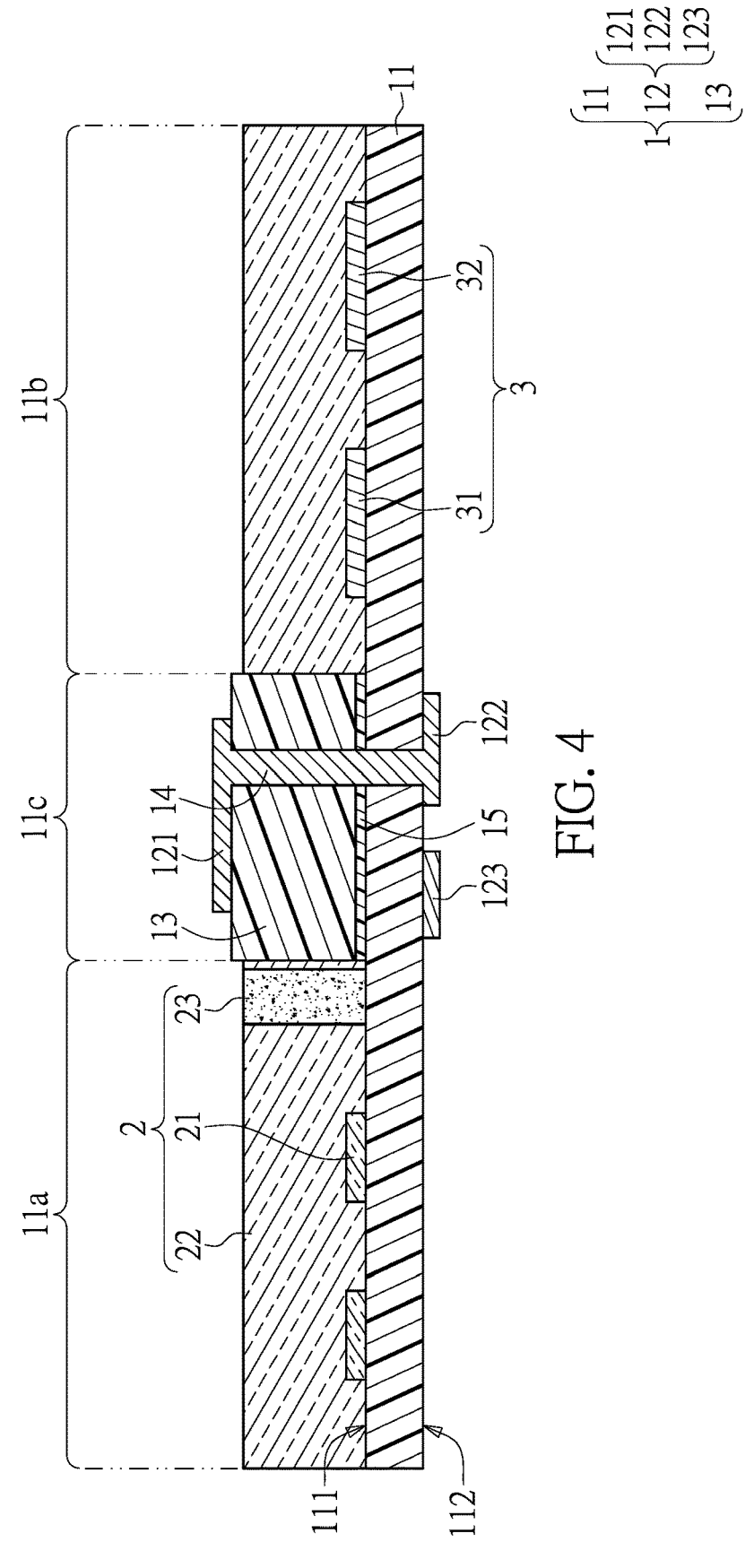
FIG. 4 is a schematic cross-sectional view taken along line IV-IV of FIG. 3.

Referring to FIG. 3 and FIG. 4, the light emitting module 2 includes a blocking wall 23 disposed between the light emitting unit 21 and the protrusion 13. Accordingly, light emitted by the light emitting unit 21 can be more effectively prevented from transmitting to the detecting unit 31 in an unexpected manner, such as not being reflected back by the organism to be detected. The blocking wall 23 can be embedded in the first packaging layer 22, and can include a black light absorbing material to be substantially opaque. That is, the blocking wall 23 has a light transmittance of less than 5% with respect to the light emitted by the light emitting unit 21.

Second Embodiment

Figure 5:
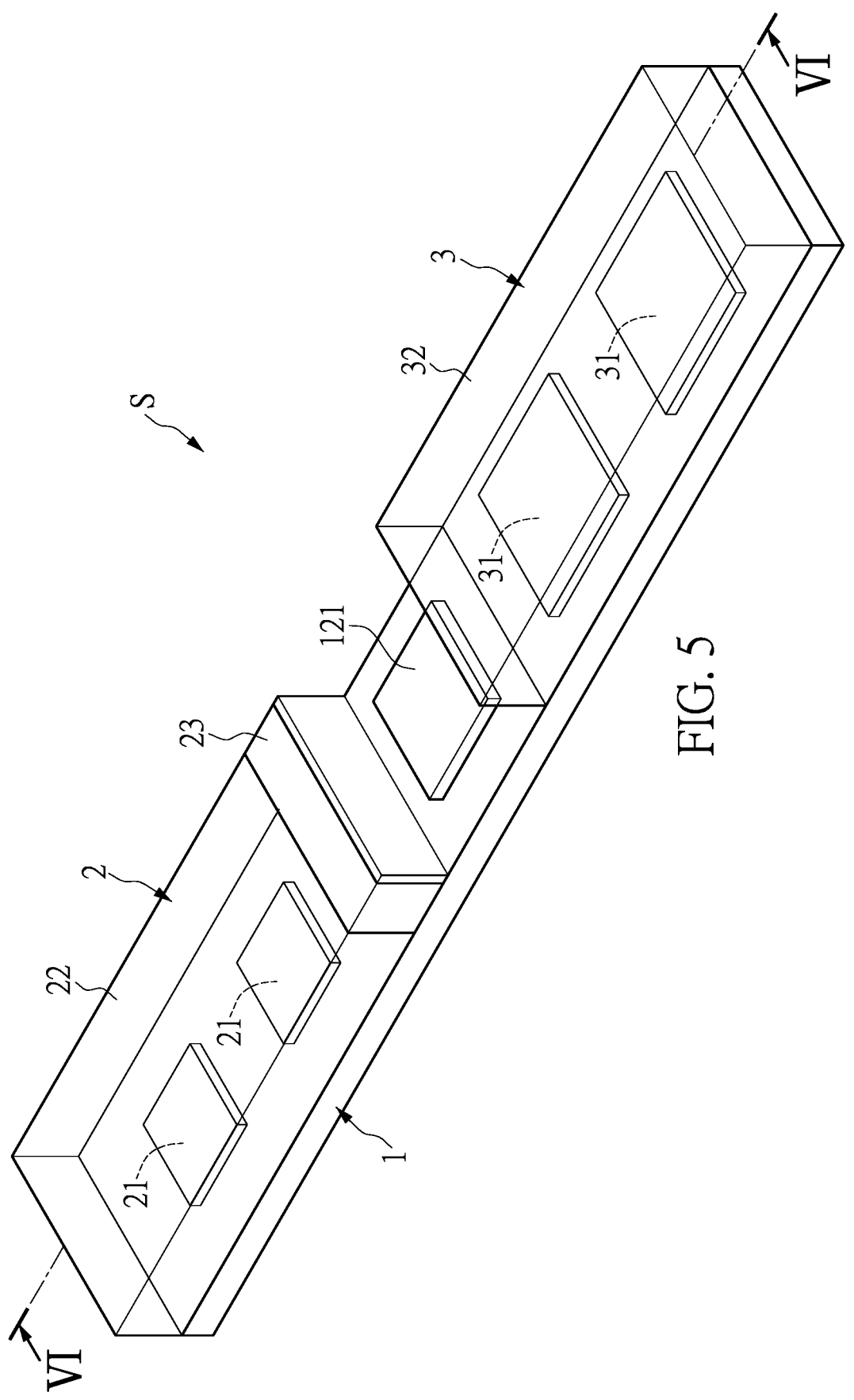
FIG. 5 is a schematic perspective view of an optical physiological sensor according to a second embodiment of the present disclosure.
Figure 6:
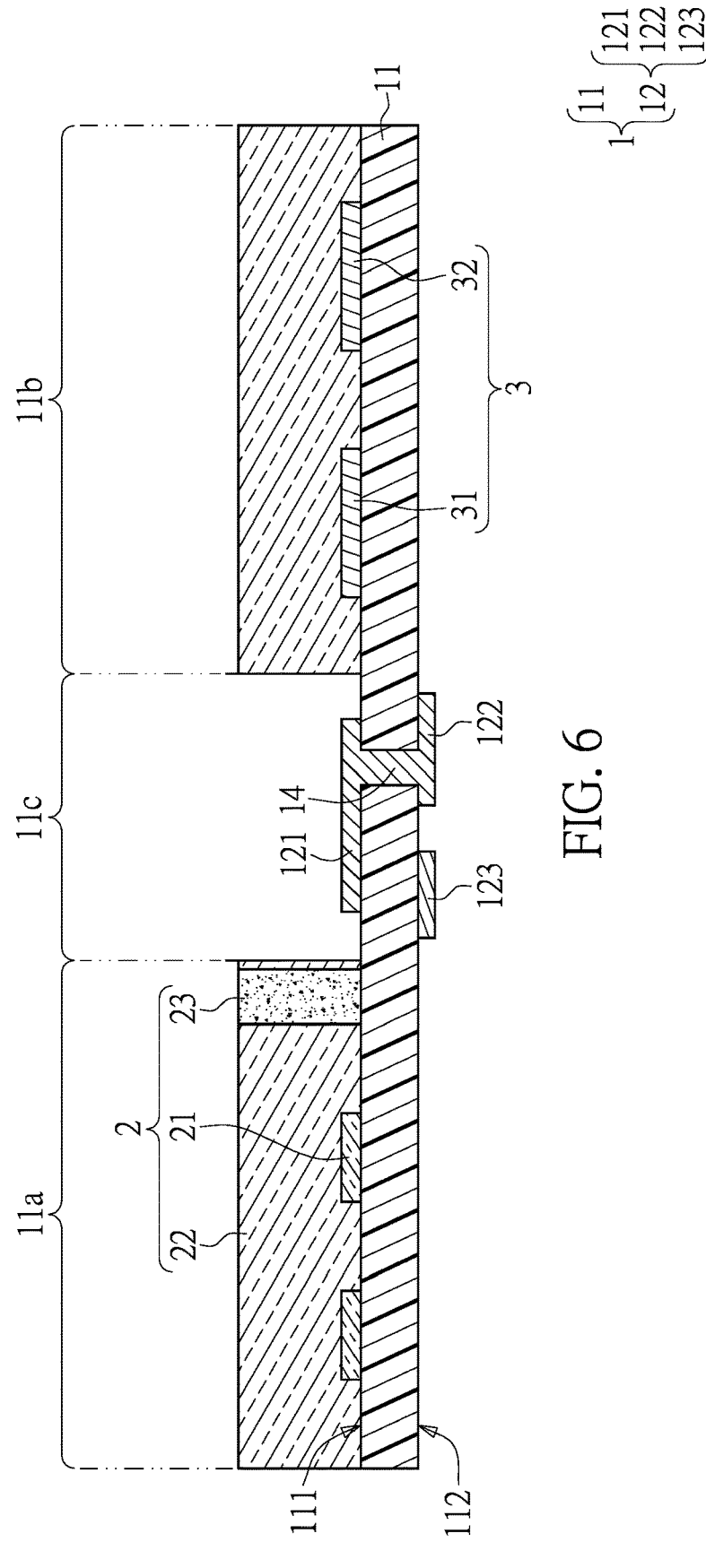
FIG. 6 is a schematic cross-sectional view taken along line VI-VI of FIG. 5.

Referring to FIG. 5 and FIG. 6, a second embodiment of the present disclosure provides an optical physiological sensor S, which includes a module substrate 1, a light emitting module 2, and a detecting module 3. The module substrate 1 includes a substrate 11, an electrode group 12, and a conductive path. The substrate 11 has an emitting area 11a, a receiving area 11b, and an organism contact area 11c between the emitting area 11a and the receiving area 11b. The electrode group 12 is disposed on the organism contact area 11c of the substrate 11, and includes a first contact electrode 121, a second contact electrode 122, and a grounding electrode 123. The conductive path is configured to provide electrical conduction between the first contact electrode 121 and the second contact electrode 122. The light emitting module 2 is disposed on the emitting area 11a, and includes at least one light emitting unit 21 and a first packaging layer 22 covering the at least one light emitting unit 21. The detecting module 3 is disposed on the receiving area 11b, and includes at least one detecting unit 31 and a second packaging layer 32 covering the at least one detecting unit 31.

The present embodiment is different from the first embodiment in that the electrode group 12 and the conductive path are directly constructed on the module substrate 1, and the light emitting module 2 includes a blocking wall 23 disposed between the light emitting unit 21 and the electrode group 12. Accordingly, light emitted by the light emitting unit 21 can be prevented from transmitting to the detecting unit 31 in an unexpected manner, such as not being reflected back by the organism to be detected. More specifically, the first contact electrode 121 is disposed on the first surface 111 of the organism contact area 11c, the second contact electrode 122 and the grounding electrode 123 are disposed on the second surface 112 of the organism contact area 11c, and the conductive path passes through the organism contact area 11c. In practice, the module substrate 1 has a conductive hole 14 that penetrates through the organism contact area 11c of the substrate 11, and the conductive hole 14 is located between the first contact electrode 121 and the second contact electrode 122 to form the conductive path. In addition, the blocking wall 23 can be embedded in the first packaging layer 22, and can include a black light absorbing material to be substantially opaque. That is, the blocking wall 23 has a light transmittance of less than 5% with respect to the light emitted by the light emitting unit 21.

The relevant technical details mentioned in the first embodiment are still valid in the present embodiment, and will not be repeated herein for the sake of brevity. Similarly, the technical details mentioned in the present embodiment can also be applied in the first embodiment.

Figure 7:
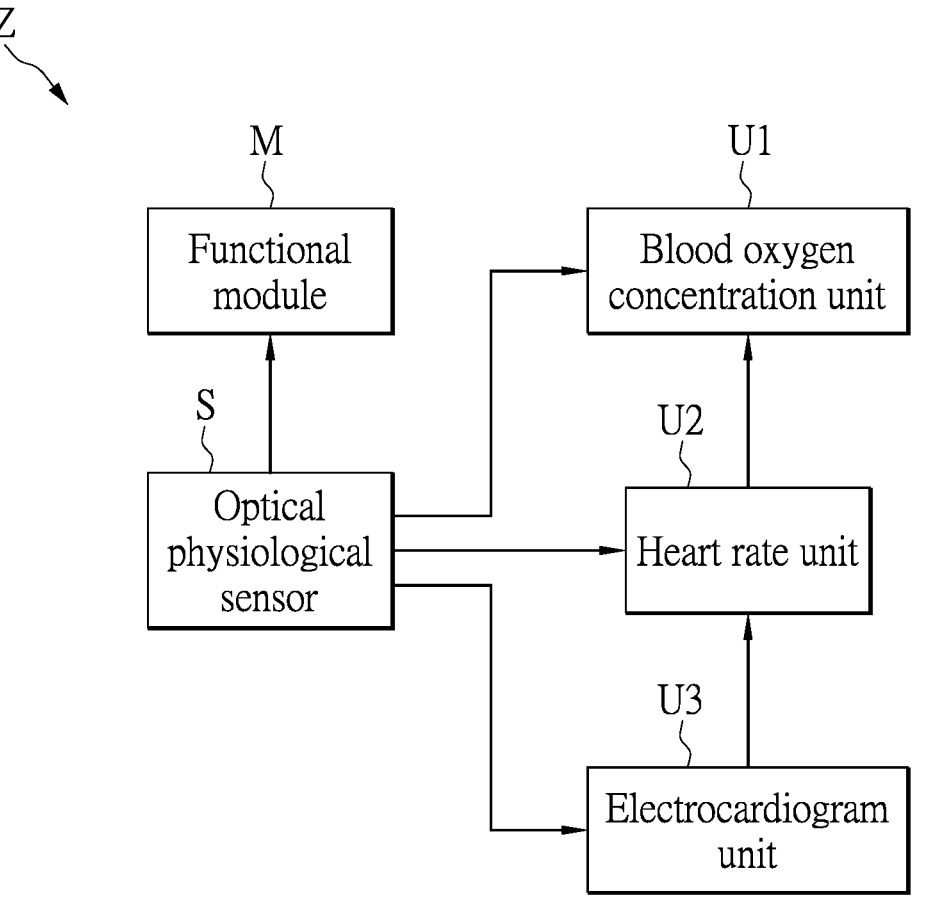
FIG. 7 is a schematic view of a health monitoring device of the present disclosure.

Referring to FIG. 7, which is to be read in conjunction with FIG. 2, FIG. 4 and FIG. 6, the present disclosure further provides a health monitoring device Z. The health monitoring device Z mainly includes a functional module M and the optical physiological sensor S mentioned in the first or second embodiment. The optical physiological sensor S is electrically connected to the functional module M. The functional module M can be put in a sleep mode under a predetermined state. When the functional module M is required to complete a certain task, the first contact electrode 121 and the second contact electrode 122 of the optical physiological sensor S can be in contact with the human body. For example, one finger is used to contact the first contact electrode 121, and another finger is used to contact the second contact electrode 122, so as to enable electrical conduction between the first contact electrode 121 and the second contact electrode 122. Accordingly, a wake-up signal is produced to activate the functional module M.

In practice, the health monitoring device Z can further include a blood oxygen unit U1, a heart rate unit U2, and an electrocardiogram unit U3 that are electrically connected to the optical physiological sensor S. The blood oxygen unit U1 can convert light signals obtained by the detecting unit 31 to corresponding information of blood oxygen concentration. The heart rate unit U2 can convert the light signals obtained by the detecting unit 31 to corresponding information of heartbeat. The electrocardiogram unit U3 can obtain ECG signals of the human body by the electrode group 12.

Beneficial Effects of the Embodiments

In conclusion, in the optical physiological sensor and the health monitoring device provided by the present disclosure, by virtue of the substrate having an emitting area, a receiving area, and an organism contact area between the emitting area and the receiving area, the electrode group being disposed on the organism contact area and including a first contact electrode, a second contact electrode, and a grounding electrode, the conductive path being configured to provide electrical conduction between the first contact electrode and the second contact electrode, the light emitting module being disposed on the emitting area, and the detecting module being disposed on the receiving area, optical sensing and contact sensing (or contact wake-up) functions can be combined in the same module. Furthermore, the optical physiological sensor and the health monitoring device have the advantages of small footprint and high flexibility.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An optical physiological sensor, comprising:
   a module substrate including:
      a substrate having an emitting area, a receiving area, and an organism contact area between the emitting area and the receiving area;
      an electrode group disposed on the organism contact area and including a first contact electrode, a second contact electrode, and a grounding electrode; and
      a conductive path configured to provide electrical conduction between the first contact electrode and the second contact electrode;
   a light emitting module disposed on the emitting area and including at least one light emitting unit and a first packaging layer that covers the at least one light emitting unit; and
   a detecting module disposed on the receiving area and including at least one detecting unit and a second packaging layer that covers the at least one detecting unit;
   wherein the substrate has a first surface and a second surface opposite to the first surface, the module substrate includes a protrusion disposed on the first surface of the organism contact area, and a height of the protrusion is greater than a height of the first packaging layer and the second packaging layer; wherein the first contact electrode is disposed on a surface of the protrusion distant from the first surface, the second contact electrode and the grounding electrode are disposed on the second surface of the organism contact area, and the conductive path passes through the organism contact area of the substrate and the protrusion.

2. The optical physiological sensor according to claim 1, wherein the protrusion is bonded to the first surface of the organism contact area by an adhesive layer.

3. The optical physiological sensor according to claim 1, wherein the light emitting module includes a blocking wall disposed between the at least one light emitting unit and the protrusion, the at least one light emitting unit is configured to emit working light, and the blocking wall has a light transmittance of less than 5% with respect to the working light.

4. The optical physiological sensor according to claim 3, wherein the blocking wall is embedded in the first packaging layer.

5. The optical physiological sensor according to claim 1, wherein the module substrate has a conductive hole that penetrates through the organism contact area of the substrate and the protrusion, and the conductive hole is located between the first contact electrode and the second contact electrode to form the conductive path.

6. The optical physiological sensor according to claim 5, wherein the light emitting module includes a blocking wall disposed between the at least one light emitting unit and the protrusion, the at least one light emitting unit is configured to emit working light, and the blocking wall has a light transmittance of less than 5% with respect to the working light.

7. The optical physiological sensor according to claim 6, wherein the blocking wall is embedded in the first packaging layer.

8. An optical physiological sensor, comprising:
   a module substrate including:
      a substrate having an emitting area, a receiving area, and an organism contact area between the emitting area and the receiving area;
      an electrode group disposed on the organism contact area and including a first contact electrode, a second contact electrode, and a grounding electrode; and
      a conductive path configured to provide electrical conduction between the first contact electrode and the second contact electrode;
   a light emitting module disposed on the emitting area and including at least one light emitting unit and a first packaging layer that covers the at least one light emitting unit; and
   a detecting module disposed on the receiving area and including at least one detecting unit and a second packaging layer that covers the at least one detecting unit;
   wherein the substrate has a first surface and a second surface opposite to the first surface, the first contact electrode is disposed on the first surface of the organism contact area, the second contact electrode and the grounding electrode are disposed on the second surface of the organism contact area, and the conductive path passes through the organism contact area of the substrate.

9. The optical physiological sensor according to claim 8, wherein the light emitting module includes a blocking wall disposed between the at least one light emitting unit and the first contact electrode, the at least one light emitting unit is configured to emit working light, and the blocking wall has a light transmittance of less than 5% with respect to the working light.

10. The optical physiological sensor according to claim 9, wherein the blocking wall is embedded in the first packaging layer.

11. The optical physiological sensor according to claim 8, wherein the module substrate has a conductive hole that penetrates through the organism contact area of the substrate, and the conductive hole is located between the first contact electrode and the second contact electrode to form the conductive path.

12. The optical physiological sensor according to claim 11, wherein the light emitting module includes a blocking wall disposed between the at least one light emitting unit and the first contact electrode, the at least one light emitting unit is configured to emit working light, and the blocking wall has a light transmittance of less than 5% with respect to the working light.

13. The optical physiological sensor according to claim 12, wherein the blocking wall is embedded in the first packaging layer.

14. A health monitoring device, comprising a functional module and the optical physiological sensor as claimed in claim 1, the functional module being electrically connected to the optical physiological sensor, wherein, when the first contact electrode and the second contact electrode are in conduction with each other, the optical physiological sensor produces a wake-up signal to activate the functional module.

* * * * *